United States Patent [19]

Hölzle et al.

[11] Patent Number: 4,497,741
[45] Date of Patent: Feb. 5, 1985

[54] WATER-SOLUBLE ZINC AND ALUMINIUM PHTHALOCYANINES

[75] Inventors: Gerd Hölzle, Liestal; Mirella Miotto, Basel; Gerhard Reinert, Allschwil; Rudolf Polony, Basel, all of Switzerland

[73] Assignee: Ciba-Geigy Corporation, Ardsley, N.Y.

[21] Appl. No.: 445,784

[22] Filed: Dec. 1, 1982

[30] Foreign Application Priority Data

Dec. 9, 1981 [CH] Switzerland ............... 7871/81

[51] Int. Cl.$^3$ ............................................. C09B 47/04
[52] U.S. Cl. ..................... 260/245.77; 8/101; 260/242.2; 260/245.1; 260/245.73; 260/245.76; 260/245.78; 260/245.79; 260/245.8
[58] Field of Search ............ 260/242.2, 245.1, 245.73, 260/245.76, 245.77, 245.79, 245.8

[56] References Cited

U.S. PATENT DOCUMENTS

| | | | |
|---|---|---|---|
| 3,134,761 | 5/1964 | Ackermann | 260/146 |
| 3,210,345 | 10/1965 | Gamlen | 260/242 |
| 3,927,967 | 12/1975 | Speakman | 8/103 |
| 4,240,920 | 12/1980 | de Luque | 252/99 |
| 4,255,273 | 3/1981 | Sakkali | 252/102 |
| 4,256,597 | 3/1981 | Sakkali | 252/99 |
| 4,256,598 | 3/1981 | Sakkali | 252/99 |
| 4,318,883 | 3/1982 | Polony et al. | 422/22 |
| 4,368,053 | 1/1983 | Eckhardt et al. | 260/245.78 X |
| 4,397,649 | 8/1983 | Springer | 260/245.8 X |

FOREIGN PATENT DOCUMENTS 1063750 3/1967 United Kingdom .
1309621 3/1973 United Kingdom .

Primary Examiner—Richard L. Raymond
Attorney, Agent, or Firm—Edward McC. Roberts

[57] ABSTRACT

The invention relates to novel zinc and aluminium phthalocyanine compounds of the formula

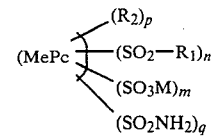

wherein MePc is the zinc or aluminium phthalocyanine ring system, M is hydrogen or a salt-forming cation, $P_1$ is hydrogen or a group of the formula —NH—CN or NH—SO$_2$R$_3$ or the salts thereof, wherein R$_3$ is alkyl, aryl or a heterocyclic ring system, R$_2$ is a neutral, non-solubilizing substituent, n is 1 to 4 and each of m and q is 0 to 3 and p is 0 to 4. These compounds are prepared by starting from the corresponding sulfohalides. The novel compounds are used as photoactivators, especially for bleaching and removing stains from textiles and for combating microorganisms in or on organic or inorganic substrates. The invention also relates to bleaching, detergent and soaking and microbicidal compositions which contain the novel phthalocyanine compounds.

8 Claims, No Drawings

WATER-SOLUBLE ZINC AND ALUMINIUM PHTHALOCYANINES

The present invention relates to novel water-soluble zinc and aluminium phthalocyanines, to the preparation thereof, to the use thereof as photoactivators, in particular for bleaching and removing stains from textiles and for combating microorganisms in or on organic or inorganic substrates, as well as to bleaching, detergent and soaking compositions and microbicidal compositions which contain the novel phthalocyanine compounds.

Various copper, nickel and cobalt phthalocyanines are known from the literature which contain sulfinic acid, cyanimide or disulfimide groups and which are used as water-soluble dyes. Reference is made in this connection to the following publications: German Offenlegungsschrift specifications 1 569 783, 1 569 729, 2 021 257, 1 794 298 and 1 419 840 as well as published European patent application 24 677. The dyes described in these publications, however, cannot be used as photoactivators and therefore cannot be used as effective bleaching agents and microbicides.

Also known are different phthalocyanine compounds, including zinc and aluminium complexes, as well as methods of bleaching textiles with these compounds as useful photoactivators, and in addition compositions which contain these compounds. In this connection, the following publications are cited by way of reference: U.S. Pat. Nos. 3,927,967, 4,033,718, 4,166,718, 4,094,806 and 4,077,768, British patent specification Nos. 1,372,035 and 1,408,144 and published European patent application Nos. 3149, 3371 and 3861.

A method of combating microorganisms on different substrates with the above mentioned water-soluble phthalocyanine compounds, e.g. water-soluble zinc and aluminium phthalocyanine compounds, and also a composition containing said compounds, is disclosed in U.S. Pat. No. 4,318,883.

It is the object of the present invention to provide water-soluble phthalocyanine compounds which may be used as photoactivators and which are particularly effective, economical and in many respects more advantageous than those already known from the literature. In particular, the novel compounds shall have especially good and effective properties as regards their action in bleaching and removing stains from textiles and in their use as microbicides. Furthermore, it shall be possible to use the novel compounds in conventional detergents and cleansing agents without adversely affecting the action of other components. Finally, the compounds of the invention shall be easily obtainable and economic to prepare.

Surprisingly, it has been found that zinc and aluminium phthalocyanine compounds which are substituted by cyanimide, disulfimide or sulfinic acid groups meet the above requirements and that the above object is thus most advantageously accomplished.

The novel phthalocyanine compounds of this invention have the general formula

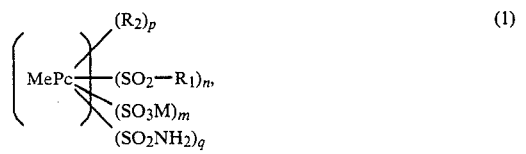

wherein MePc is the zinc or aluminium phthalocyanine ring system, M is hydrogen or the equivalent of a salt-forming cation, $R_1$ is hydrogen, M or a group of the formula

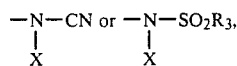

wherein X is hydrogen or ammonium or the equivalent of a monovalent, divalent or trivalent metal ion, and $R_3$ is unsubstituted or substituted alkyl, unsubstituted or substituted aryl or an unsubstituted or substituted and/or fused aromatic heterocyclic ring; $R_2$ is a neutral, non-solubilising substituent, n has any value from 1 to 4, each of m and q has any value from 0 to 3 and p has any value from 0 to 4, while the sum of n+m and n+q in each case is 1 to 4 and q is only different from 0 if $R_1$ is a group of the formula

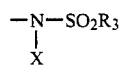

and m is 0, and the substituents $R_2$ present in the molecule may be the same or different. The term aryl denotes mononuclear or polynuclear aromatic ring systems, preferably phenyl, 1-naphthyl or 2-naphthyl, most preferably phenyl. In composite groups (see also below), aryl has the same definition.

Examples of suitable heterocyclic aromatic rings (substituent $R_3$) are 5- or 6-membered aromatic heterocyclic rings which contain 1 to 2 heteroatoms selected from the group consisting of nitrogen, oxygen and sulfur as ring members, and which may contain a fused benzene or naphthalene ring. Examples of such rings are the furan, benzofuran, thiophene, benzthiophene, benzoxazole, thiazole, benzthiazole, benzimidazole, pyridine or quinoline ring. Heterocyclic ring systems which contain fused benzene or naphthalene rings may also of course be linked through the fused ring to the $SO_2$ group.

The aryl radicals and the heteroaromatic rings (including those with fused benzene rings) may be substituted by different radicals, e.g. by 1 to 3 substituents, preferably by one substituent. Examples of such substituents are: alkyl or alkoxy, nitro, haloalkyl, halogen, alkoxycarbonyl, cyano, alkylsulfonyl, acylamino, carboxy and derivatives thereof, sulfo and derivatives thereof, acyloxy, trifluoromethyl and dialkylamino.

Halogen is preferably fluorine, chlorine or bromine, with chlorine being most preferred. Representative examples of derivatives of carboxyl and sulfo groups are their salts, esters and amides.

Examples of preferred substituents of alkyl groups $R_3$ are: hydroxy, alkoxy, halogen, cyano, aryl (especially phenyl or naphthyl, unsubstituted or substituted like the aryl groups $R_3$), carbalkoxy, aminocarbonyl or dialkylamino.

Alkyl and alkoxy groups by themselves or as moieties of other groups contain e.g. 1 to 8, preferably 1 to 6 and, most preferably, 1 to 4, carbon atoms. Alkyl moieties of carboxyl or carboxamide groups or of sulfonamide groups contain preferably 1 to 8 carbon atoms.

$R_2$ may be any neutral, non-solubilising substituent common in phthalocyanine chemistry. $R_2$ is preferably halogen, aryl (e.g. phenyl) or cyano, and is in particular chlorine, bromine or iodine, with chlorine being most preferred.

The sulfo groups or sulfino groups —SO₂R₁ in the phthalocyanine ring may be in the free form or in salt form. M is therefore hydrogen or a salt-forming cation. Preferred salt-forming cations are alkali metal ions, alkaline earth metal ions, ammonium ions and amine salt ions (i.e. substituted ammonium ions which are derived from primary, secondary or tertiary amines). In particular, M is hydrogen, an alkali metal ion, ammonium ion or amine salt ion, and is most preferably hydrogen, sodium, potassium or ammonium. Amine salt ions (substituted ammonium ions) are e.g. those of the formula

wherein each of $R_4$, $R_5$ and $R_6$ independently of the other is hydrogen or alkyl (preferably of 1 to 4 carbon atoms) which is unsubstituted or substituted by halogen, hydroxy, phenyl or cyano, with the proviso that at least one substituent R is different from hydrogen. Two radicals R when taken together may also complete a saturated 5- or 6-membered nitrogen-containing heterocyclic ring which may also additionally contain an oxygen atom or a nitrogen atom as ring member. Examples of such heterocyclic rings are: piperidine, piperazine, morpholine, pyrrolidine, imidazolidine etc.

The groups —NH—CN and —NH—SO₂—R₃ as substituent $R_1$ may also be in the free form or in salt form. In addition to being hydrogen, X is ammonium or the equivalent of a monovalent, divalent or trivalent metal ion. X is preferably hydrogen, ammonium or an alkali metal ion, e.g. a sodium or potassium ion.

The indices n, m, p and q (provided m, q and/or p are not already zero), may be any values in the indicated range. As is customary in phthalocyanine chemistry, the individual products frequently consist of mixtures, as homogeneous products are not always obtained in their preparation (sulfonation, sulfochlorination, halogenation etc). The indices therefore indicate the "degree of substitution", which does not, of course, have to be a whole number.

The number of water-solubilising groups which must be present in the molecule, i.e. groups of the formula —SO₂R₁+sulfo groups, also depends on the number of substituents $R_2$ present. The number of the first mentioned groups present in the molecule should at all events be such as to ensure a sufficient water-solubility. A minimum solubility of 0.01 g/l may be sufficient; but in general a solubility of 0.1 to 20 g/l is desirable.

As is known from phthalocyanine chemistry, the third valency of the aluminium in the aluminium phthalocyanine ring system is saturated by an additional ligand, e.g. an anion. This anion may be identical with the anion of the aluminium compound which has been used for preparing the complex. Examples of such anions are halide, sulfate, nitrate, acetate or hydroxyl ions.

As is also known from phthalocyanine chemistry, the substituents —SO₂R₁, R₂ and —SO₃M and —SO₂NH₂ are bound preferably in the 3- and/or 4-positions of the carbocyclic aromatic rings of the phthalocyanine ring system. However, other positions too may also carry these substituents.

Phthalocyanine compounds of the formula (1) which merit special mention are those wherein M is hydrogen, an alkali metal ion, ammonium ion or amine salt ion, $R_2$ is a halogen atom or cyano, X is hydrogen or an ammonium or alkali metal atom, $R_3$ is alkyl or alkyl substituted by hydroxy, halogen, alkoxy, cyano, phenyl, carbalkoxy, dialkylamino or aminocarbonyl; phenyl or naphthyl, each unsubstituted or substituted by alkyl, alkoxy, halogen, nitro, alkylsulfonyl, dialkylamino, cyano, sulfo or carboxy, or their derivatives, or is a 5- or 6-membered aromatic heterocyclic ring which contains 1 or 2 heteroatoms selected from the group consisting of nitrogen, oxygen and sulfur and which may be unsubstituted or substituted and/or may carry a fused benzene or naphthalene ring, and the sum of n+m or n+q is 2 to 4 in each case.

Particularly interesting compounds of the formula (1) are those wherein $R_2$ is a halogen atom and $R_3$ is $C_1$–$C_4$alkyl, $C_1$–$C_4$haloalkyl, $C_2$–$C_6$alkoxyalkyl, $C_1$–$C_4$hydroxyalkyl, $C_2$–$C_5$cyanoalkyl, di($C_1$–$C_4$)alkylamino($C_1$–$C_4$)alkyl or benzyl, phenyl or phenyl substituted by 1 to 3 substituents selected from the group consisting of halogen, $C_1$–$C_4$alkyl, $C_1$–$C_4$alkoxy, cyano, nitro, di($C_1$–$C_4$)alkylamino, and sulfo and carboxy and the salts thereof; more particularly those compounds of the formula

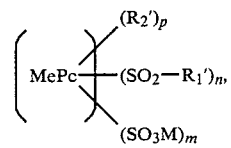

wherein $R_2'$ is chlorine, bromine or iodine, preferably chlorine, M' is hydrogen, sodium, potassium or ammonium, and $R_1'$ is hydrogen, M' or a group of the formula

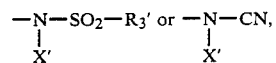

wherein X' is hydrogen, sodium, potassium or ammonium, and $R_3'$ is $C_1$–$C_4$alkyl, phenyl or $C_1$–$C_4$alkylphenyl, chlorophenyl or methoxyphenyl, and MePc, n, m and p are as defined for formula (1).

Preferred compound of the formula (2) are those wherein $R_2'$ is chlorine, M' is hydrogen, sodium or potassium, X' is hydrogen, sodium or potassium, $R_3'$ is $C_1$–$C_4$alkyl, phenyl or $C_1$–$C_4$alkylphenyl, p is a value from 0.5 to 1.5, n is a value from 2 to 4 and m is 0; in particular those wherein $R_2'$ is chlorine, M' is hydrogen or sodium, $R_1'$ is a

group, wherein X" is hydrogen or sodium, p is a value from 0.5 to 1.5, n is a value from 3 to 4 and m is 0.

Preferred compounds of the formula (1) are also those wherein q is 0.

Particularly useful phthalocyanine compounds of the formulae (1) and (2) are those in which $R_1$ and $R_1'$ are hydrogen or a group of the formula

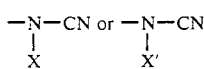

respectively, preferably the group of the formula

The phthalocyanine compounds of this invention may be prepared by methods which are known per se. It is convenient to prepare compounds of the formula (1) by reacting one molar equivalent of a phthalocyanine sulfohalide of the formula

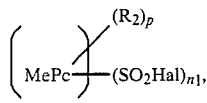 (3)

wherein MePc, $R_2$ and p are as defined for formula (1), Hal is a halogen atom, preferably a chlorine atom, and $n_1$ is any value from 1 to 4, (a) with $n_1'$ molar equivalents of cyanamide or a salt thereof, or (b) with $n_1'$ molar equivalents of ammonia, and reacting the resultant sulfonamide with $n_1$ or $n_1''$ molar equivalents of a halide of the formula Hal—$SO_2$—$R_3$ wherein Hal is as defined above and $R_3$ is as defined for formula (1), or (c) with $n_1'$ molar equivalents of a compound of the formula $H_2N$-Y, wherein Y is amino, unsubstituted or substituted alkylamino or dialkylamino, cyclohexylamino or N-acylamino, preferably with hydrazine, where $n_1'$ and $n_1''$ are each a value $\leq n_1$, whilst in (b) $n_1$ molar equivalents of ammonia are used if the reaction is carried out with $n_1''$ molar equivalents of Hal—$SO_2$—$R_3$, and, in products obtained according to (a) to (c) which still contain sulfohalide groups simultaneously or subsequently hydrolysing these latter to sulfo groups, and, if desired, converting resultant compounds into the corresponding salts or converting resultant salts into the corresponding free acids.

To prepare phthalocyanine compounds of the formula (1), wherein $R_1$ is a group of the formula —NX-$SO_2$—$R_3$, in particular those of the formula

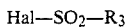 (4)

a start is conveniently made from compounds of the formula (3), in particular from those of the formula

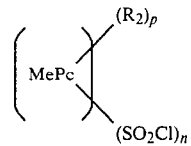 (5)

and 1 molar equivalent of such a compound is reacted with $n_1'$ or n molar equivalents of ammonia, and the resultant sulfonamide is reacted with $n_1'$, n or $n_1''$ molar equivalents of a sulfohalide of the formula Hal—$SO_2$—$R_3$, in particular with a sulfochloride of the formula Cl—$SO_2$—$R_3$. Resultant compounds containing unreacted sulfochloride groups are subsequently hydrolysed and, if desired, compounds in which M or X is hydrogen are converted into salts. If the compound of the formula (5) is reacted first with n molar equivalents of ammonia and then with $n_1''$ molar equivalents of the sulfohalide, compounds of the formula (1) are obtained in which m is 0 and q≠0.

The reaction is preferably carried out in the temperature range from about 0° to 100° C., most preferably from 30° to 50° C., in aqueous or organic aqueous medium, and at a pH above 7, preferably at a pH of about 10, to give the corresponding salts. It is preferred to adjust the pH by addition of alkalies such as alkali metal hydroxides or alkali metal carbonates.

The salts of the compounds obtained, especially the alkali salts, are usually readily soluble in water and are isolated from the reaction mixture by salting out. The more reluctantly soluble free acids are isolated by acidification with strong mineral acids.

Suitable organic solvents which may concurrently be used are alcohols such as methanol, ethanol or propanol; ketones such as acetone; amides such as formamide or dimethylformamide; dimethylsulfoxide; tetrahydrofuran; chlorinated hydrocarbons such as chloroform; and aromatic hydrocarbons such as benzene or toluene.

Alternatively, the compounds of the formula (1) in which $R_1$ is —NX—$SO_2$—$R_3$ may also be prepared by reacting phthalocyanine sulfohalides (especially sulfochlorides) of the formula (3) with sulfonamides of the formula $R_3$—$SO_2$—$NH_2$. Preferred reaction parameters correspond to those specified for the above described process.

To prepare phthalocyanine compounds of the formula (1), wherein $R_1$ is a —NX—CN group, in particular those of the formula

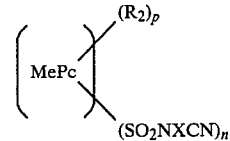 (6)

a start is conveniently made from compounds of the formula (3), in particular from those of the formula (5), and 1 molar equivalent of such a compound is reacted with $n_1'$ or n molar equivalents of cyanamide or a salt thereof. Resultant compounds with unreacted sulfochloride groups are subsequently hydrolysed and, if desired, compounds in which M or X is hydrogen are converted into salts.

The reaction is preferably conducted in aqueous medium or in an inert organic solvent which is preferably miscible with water, or in a mixture of water and an organic solvent, at a pH in the range from 4 to 14, in particular from 9 to 14, and in the temperature range from −10° to +110° C., in particular from 0° to 40° C. Examples of water-miscible solvents are a lower alcohol such as methanol or ethanol, N-methylpyrrolidone, dimethylformamide, dimethylsulfoxide or mixtures thereof.

Cyanamide may also be used in the form of a salt thereof, for example as monosodium or disodium cyanamide or calcium cyanamide.

Bases (acid acceptors) which may be used in the condensation reaction of a phthalocyanine sulfohalide with cyanamide or a salt thereof, or with an amide of the formula $R_3$—$SO_2$—$NH_2$ or with a phthalocyanine sulfonamide (from a halide+ammonia) with a halide of the formula $R_3$—$SO_2$—Hal for obtaining compounds of the general formula (1), are preferably alkali metal hydroxides and alkaline earth metal hydroxides and basic salts of alkali metals and alkaline earth metals with inorganic or organic acids or tertiary organic bases. The preferred alkali metals are sodium and potassium and the preferred alkaline earth metal is calcium. Basic salts are preferably the alkali metal salts of carbonic acid, phosphoric acid and acetic acid, e.g. in particular sodium and potassium bicarbonate, sodium and potassium carbonate, sodium dihydrogen phosphate, disodium hydrogen phosphate, trisodium phosphate or the corresponding potassium salts. Tertiary organic bases are e.g. pyridine, triethanolamine or dimethyl aniline.

To prepare phthalocyanine compounds of the formula (1), wherein $R_1$ is hydrogen, a start is likewise made from the sulfohalides of the formula (3), which are reacted with a hydrazine derivative of the formula $H_2N$-Y, wherein Y is amino, unsubstituted or substituted alkylamino or dialkylamino, cyclohexylamino or N-acylamino, preferably with hydrazine itself. This reaction too is preferably conducted in aqueous medium. For example, the reaction may be carried out in the pH range from 5 to 14 (see Examples 5, 5.1 and 5.2).

Alternatively, the sulfohalide (in particular sulfochloride) groups of the phthalocyanine sulfohalides (in particular sulfochlorides) used as starting materials may also be reacted in accordance with the following reaction scheme

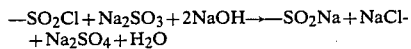
—$SO_2Cl + Na_2SO_3 + 2NaOH \rightarrow$—$SO_2Na + NaCl + Na_2SO_4 + H_2O$ to give the corresponding sulfino groups. This method can also be employed for the preparation of the phthalocyanine compounds of the formula (1), wherein $R_1$ is hydrogen or M. It may be carried out in accordance with the procedure described in Houben-Weyl, Vol. 9, page 299 et seq. (1955).

As is evident from the general description of the process, compounds of the formula (1), wherein m is not zero, are obtained by converting some of the sulfochloride groups of the starting compounds into sulfonic acid groups by hydrolysis, during or after the conversion of the —$SO_2Cl$ groups into —$SO_2R_1$ groups. Accordingly, the main reaction may be carried out e.g. such that, simultaneously with the reaction, some of the sulfochloride groups are hydrolysed, or the procedure may be such that initially an amount of cyanamide, halide of the formula Hal—$SO_2R_3$ or compound of the formula $H_2N$-Y insufficient for the complete reaction of all sulfochloride groups is reacted and subsequently the remaining sulfochloride groups are hydrolysed by a special reaction step in acid or alkaline medium, e.g. in a pH range from 1 to 4 or from 8 to 12, if desired with heating, e.g. in the temperature range from 20° to 60° C.

The phthalocyanine compounds obtained by the above described processes are isolated in conventional manner by salting out, e.g. with sodium, potassium or ammonium chloride, and/or by acidification with a mineral acid, or by concentrating the neutral or weakly acid aqueous solutions of these compounds, preferably at moderately elevated temperature and under reduced pressure. The phthalocyanine compounds of the invention are accordingly obtained in the form of their sodium, potassium or ammonium salts, or in the form of their acids, or in a mixture of these forms.

If it is desired to obtain compounds of the formula I, wherein $m \neq 0$, it is of course also possible to use starting compounds which already contain sulfo groups in addition to sulfochloride groups (and/or $R_2$ groups).

Substituents $R_2$, especially halogen atoms, may also be introduced subsequently by halogenation into compounds of the formula (1), wherein p is 0.

The starting sulfohalides (sulfochlorides) of the formula (3) or (5) may be prepared by known methods by reacting zinc and aluminium phthalocyanines which may also already contain substituents $R_2$ with a halosulfonic acid, preferably with chlorosulfonic acid. Such reactions are described in detail in the literature relating to phthalocyanines.

The synthesis of the phthalocyanine ring structure from derivatives of phthalic acid to give chlorinated phthalocyanines is described in Ullmann's Encyclopädie der technischen Chemie, 4th Edition, Vol. 18, page 507 et seq. and by F. H. Moser and A. L. Thomas, "Phthalocyanines" (1963), page 104 et seq. Halogenated phthalocyanines or phthalocyanines which contain other inert substituents may be obtained by co-condensation of unsubstituted or correspondingly substituted phthalic acids or derivatives thereof by known methods customarily employed in phthalocyanine chemistry. Synthesis of the phthalocyanine ring structure from phthalic anhydride or phthalodinitrile in the presence of a chloride, e.g. $AlCl_3$ or $ZnCl_2$, gives already chlorinated phthalocyanines, in particular those containing 0.5 to 1.5 moles of chlorine per mole of aluminium phthalocyanine.

The phthalocyanines of this invention may be used, as stated at the outset, as photoactivators, in particular for combating microorganisms, but most particularly for bleaching and removing stains from textiles. In the literature the term "photosensitiser" is often used instead of "photoactivator" and may therefore be considered as standing equally well for the latter term used throughout this specification.

The bleaching and stain removing method of this invention which comprises the use of the phthalocyanine compounds of the formula (1), i.e. the treatment of textiles with said compounds, is preferably carried out in a neutral or alkaline pH range.

The zinc or aluminium phthalocyanines of the invention are used with advantage in amounts of 0.01 to 100 mg/l, preferably 0.01 to 50 mg/l, of treatment bath. Depending on the number of water-solubilising groups and of the substituent $R_2$, the amount employed may vary.

The process is preferably carried out as a combined washing and bleaching process, in which case the aqueous bath also contains an organic detergent, such as soap or a synthetic detergent (see below), and can also contain other detergent aids, such as soil suspending agents, for example sodium carboxymethyl cellulose, complexing agents such as sodium tripolyphosphate, sodium silicate and sodium ethylenediamine tetraacetate, and fluorescent whitening agents. The photoactivator can therefore either be already incorporated in the corresponding detergent or can be added subsequently to the wash liquor. However, the process can also be carried out as a pure bleaching process without detergent aids. In this case, it is advantageous if the treatment bath contains an electrolyte, for example sodium chloride, sodium sulfate or sodium tripolyphosphate, in order to ensure the exhaustion of the water-soluble phthalocyanine dye. The amounts of electrolyte can be about 0.5 to 20 g/l.

As mentioned above, the wash and bleaching liquors may also contain one or more fluorescent whitening agents. These may be conventional detergent whiteners. However, it is preferred to use fluorescent whiteners selected from the classes of the distyrylbiphenylsulfonic acids and salts thereof and/or of the 4,4'-bis-(1,2,3-triazol-2-yl)stilbenedilsulfonic acids and salts thereof. By combining these fluorescent whitening agents with the photoactivators of the invention it is possible to obtain particularly good bleaching effects which are more intense than would be expected from the additive action of the individual components. Representative of such fluorescent whitening agents are those of the formula (A1) below, e.g. of the formula (A2), most preferably of the formula (A3). Fluorescent whitening agents of the formula (A4) also give good results, as do likewise mixtures of the fluorescent whitening agents of the formulae (A3) and (A4).

The bleaching method of this invention is conveniently carried out in the temperature range from about 20° to 100° C., especially 20° and 85° C., over a period of 15 minutes to 5 hours, preferably 15 minutes to 60 minutes.

The presence of oxygen and irradiation with light is necessary for the bleaching process of the invention. The oxygen dissolved in water or atmospheric oxygen suffices as oxygen source.

The irradiation can be effected with an artificial light source (e.g. incandescent lamp, infra-red lamp), and the bleach or washing bath can be irradiated direct, either by means of a light source inside the receptacle containing the liquor (e.g. lamp in the washing machine) or by a light source outside the receptacle. Likewise, the irradiation can be effected only when the textiles are removed from the treatment bath. In this case, the textiles should however still be moist and, if not, they must subsequently be moistened again. Sunlight can also serve as light source, in which case the textiles are exposed to sunlight either in the soaking bath or in the moist state after the treatment in the washing or bleach bath. The light source employed should preferably emit light in the range from 300 to 800 nm.

The zinc and aluminium phthalocyanines of this invention require the presence of oxygen and water as well as irradiation by light in order to exert their antimicrobial activity. For this reason, the process is carried out in general in aqueous solutions or on moist substrates, whilst the oxygen dissolved in water or atmospheric oxygen acts as oxygen source.

The irradiation can be effected with an artificial light source or with sunlight. Good effects are achieved, for example, with light in the range from about 300 to 2,500 nm. Thus irradiation can be effected e.g. with a commercially available incendescent lamp. The intensity of irradiation may vary within wide limits. It depends on the concentration of active ingredient, on the nature of the substrate, or on the substances additionally present by which the light intensity is influenced. As a further parameter, the irradiation time can be varied, i.e. to obtain the same action it is necessary to irradiate for a longer time if the light intensity is lower than if it is higher. In general, irradiation times of a few minutes up to a few hours are possible, depending on the field of application.

If the process is carried out in an aqueous bath (for example in disinfecting textiles), either the irradiation with light can be carried out direct in the treatment bath by means of an artificial light source located inside or outside the bath, or the substrates in the moist state may either be irradiated with an artificial light source in the same way or exposed to sunlight.

Good antimicrobial effects can be obtained even with only very small concentrations of active ingredient, for example with 0.001 ppm. The concentration is preferably between 0.05 and 100 and more preferably between 0.01 and 50 ppm, depending on the field of application and on the phthalocyanine derivative used. As the active ingredients are dyes, the upper concentration limit is determined by the fact that an undesired coloration of the substrates would be observed if it were exceeded. The upper concentration limit is therefore limited by the strength of the intrinsic colour of the agent used, but can be 1000 ppm or more.

The zinc phthalocyanine and aluminium phthalocyanine compounds of the formula (1) used in the process of the invention have an exceptionally broad activity spectrum against microorganisms. Accordingly, the process of the invention makes it possible to combat, in particular, Gram-positive and Gram-negative bacteria or to protect various substrates against attack by the latter. An excellent action is also observed against fungi.

In the process of the invention, it is also possible to add activity promoting substances, including electrolytes, for example inorganic salts such as sodium chloride, potassium chloride, sodium sulfate, potassium sulfate, sodium acetate, ammonium acetate, alkali metal phosphates and alkali metal tripolyphosphates, in particular sodium chloride and sodium sulfate. These salts can be added to the compositions according to the invention or direct in the application process, so that they are preferably present in a concentration of 0.1 to 10% in the application solution.

Because of the said broad activity spectrum against microorganisms, the process of this invention, or the compositions of the invention, may be used in a number of fields of application, which are mentioned below by way of exemplification.

An important application is the disinfection of textiles of synthetic or natural origin. For example, domestic or industrial laundry goods can be disinfected with the aid of the process of the invention. For this purpose, the laundry goods can be treated with aqueous solutions of water-soluble phthalocyanine derivatives, under irradiation with light, in the abovementioned manner. The phthalocyanine dye can advantageously be present in the treatment liquor in a concentration of 0.01 to 50 mg/liter. Disinfection can conveniently also be carried out together with the washing process. For this purpose, the laundry goods are treated with a wash liquor which contains conventional active detergents, one or more water-soluble zinc phthalocyanine or aluminium phthalocyanine derivatives and, if appropriate, inorganic salts and/or other substances having antimicrobial action. The washing operation can be carried out by hand, for example in a tub, or also in a washing machine. The required irradiation can be carried out during the washing process with suitable light sources, or also the moist laundry can subsequently, for example during drying, either be irradiated with a suitable artificial light source or also simply be exposed to sunlight.

The compounds of the formula (1) can be added direct to the disinfecting liquor, bleaching liquor or wash liquor. However, they can also be incorporated into soaps or washing powders which contain known mixtures of active detergents, for example soap in the form of flakes and powders, synthetics, soluble salts of sulfonic acid hemiesters of higher fatty alcohols, higher alkyl-substituted and/or alkyl-polysubstituted arylsulfonic acids, sulfocarboxylic acid esters of intermediate to higher alcohols, fatty acid acylaminoalkyl- or acylaminoaryl-glycerol-sulfonates, phosphoric acid esters of fatty alcohols and the like, so-called builders, for example alkali metal polyphosphates and polymetaphosphates, alkali metal pyrophosphates, alkali metal salts of carboxymethylcellulose and other soil redeposition inhibitors, and also alkali metal silicates, nitrilotriacetic acid, ethylenediaminetetraacetic acid, foam stabilisers such as alkanolamides of higher fatty acids, and, if appropriate, antistatic agents, fat-restorative skin protectives such as lanolin, enzymes, perfumes and dyes, fluorescent whitening agents, as well as further inorganic salts and/or further microbicides or bleaching agents.

The process of this invention may also be used for providing textiles with an antimicrobial finish, because the zinc phthalocyanine and aluminium phthalocyanine derivatives exhaust well onto the fibre and ensure a long-lasting effect.

A further field of application of the process of the invention and of the compositions of the invention is the disinfection of hospital laundry, medical utensils and equipment as well as floors, walls and furniture (surface disinfection) in general and also in hospitals in particular. The disinfection of hospital laundry can be carried out in the manner described above for general laundry. The other objects and floor and wall surfaces can be treated with aqueous solutions which contain zinc phthalocyanine or aluminium phthalocyanine compounds of formula (1) and can be irradiated at the same time, or subsequently, with suitable light sources. The disinfecting solutions can additionally contain active detergents, other microbicides and/or inorganic salts.

For surface disinfection, it is possible e.g. to apply to the particular surface an aqueous solution of the phthalocyanine compounds of the invention (for example by spraying), which solution preferably contains about 0.001–50 ppm of active ingredient. The solution may also contain other conventional additives, for example wetting agents, dispersants or emulsifiers, active detergents and, if appropriate, inorganic salts. The surface is simply exposed to sunlight after the solution has been applied, or, if required, irradiation can additionally be effected with an artificial light source, for example an incandescent lamp. It is advisable to keep the surface moist during irradiation.

The process of the invention or the compositions can also advantageously be used for disinfecting swimming baths and swimming pools. For this purpose, one or more of the phthalocyanine compounds which can be used in the process of the invention are conveniently added to the water in the swimming bath or pool, preferably in an amount from 0.001 to 50 ppm, preferably from 0.01 to 10 ppm. Irradiation is effected simply by means of sunlight. If appropriate, additional irradiation can be provided by means of built-in lamps. This process makes it possible to keep the water in swimming pools free from harmful germs and to maintain excellent water quality.

The process of the invention can also be used for the disinfection of effluents from sewage purification plants. For this purpose, for example 0.001–100 ppm, in particular 0.01–10 ppm, of one or more of the compounds of the formula (1) are added to the effluent. Irradiation is conveniently effected by means of sunlight and, if necessary, can additionally be carried out with artificial light sources.

The possible applications mentioned above are only illustrative of the very broad applicability of the process and of the compounds of the invention.

The above described process for bleaching and removing stains from textiles is preferred.

The present invention also relates to compositions for carrying out the process of the invention, in particular to microbicidal compositions and preferably to bleaching compositions, detergent compositions and soaking compositions. These compositions contain one or more zinc phthalocyanines and/or aluminium phthalocyanines of the formula (1). Depending on the type of application, the said compositions may additionally contain customary formulation components.

Preferred compositions of this type contain one or more zinc phthalocyanine and/or aluminium phthalocyanine compounds of the formula (1), one or more inorganic salts, for example NaCl, KCl, NaBr, KBr, $K_2SO_4$, $Na_2SO_4$, $K_2CO_3$, $Na_2CO_3$, $NaHCO_3$ and the like, in particular NaCl and/or $Na_2SO_4$, and, optionally, water. For example, a composition of this type consists of about 50–80% of a compound of the formula (1), in particular of the formula (2), 10–30% of NaCl and/or $Na_2SO_4$, for example 5–15% of NaCl and 5–15% of $Na_2SO_4$, and 0 to 30% of water. These compositions may also be present in aqueous solution, for example in the form of a 5–50% solution, for example a 5–20% solution.

In addition to the zinc phthalocyanine or aluminium phthalocyanine active ingredient, detergent compositions of this invention having bleaching action contain e.g. customary detergent components, for example one or more organic detergents, alkaline builder salts and, if appropriate, further bleaching agents, for example percompounds such as a perborate, percarbonate or the like.

The detergent or soaking compositions of the invention contain e.g. the known mixtures of active detergents, for example soap in the form of flakes and powders, synthetics, soluble salts of sulfonic acid half-esters of higher fatty alcohols, higher alkyl-substituted and/or alkyl-polysubstituted arylsulfonic acids, sulfocarboxylic acid esters of intermediate to higher alcohols, fatty acid acylaminoalkyl- or acylaminoarylglycerolsulfonates, phosphoric acid esters of fatty alcohols and the like. Examples of suitable so-called builders are alkali metal salts of carboxymethylcellulose and other soil redeposition inhibitors, and also alkali metal silicates, alkali metal carbonates, alkali metal borates, alkali metal perborates, alkali metal percarbonates, nitrilotriacetic acid, ethylenediaminetetraacetic acid, and foam stabilisers such as alkanolamides of higher fatty acids. The detergent compositions may further contain e.g.: antistatic agents, fat-restorative skin protectives such as lanolin, enzymes, antimicrobial agents, perfumes and fluorescent whitening agents.

The detergent or soaking compositions of the invention preferably contain the zinc phthalocyanine and/or aluminium phthalocyanine compounds of the formula (1) in an amount of 0.0005 to 1.5 percent by weight, in particular 0.005 to 1 percent by weight, based on the total detergent or soaking composition.

For example, detergent or soaking compositions of the invention with a having bleaching action contain 0.005-1% by weight of the above mentioned zinc phthalocyanine and/or aluminium phthalocyanine compounds, 10-50% by weight of an anionic, non-ionic, semi-polar, ampholytic and/or zwitterionic surface-active substance, 0-80% of an alkaline builder salt and, if desired, further customary detergent components, for example those mentioned above.

Examples of suitable surface-active substances in the said compositions are also water-soluble alkylbenzenesulfonates, alkylsulfates, alkyl ether sulfates, paraffinsulfonates, α-olefinsulfonates, α-sulfocarboxylic acids, their salts and esters, alkylglyceryl ether sulfonates, fatty acid monoglyceride sulfates or -sulfonates, alkylphenol polyethoxy ether sulfates, 2-acyloxyalkanesulfonates, β-alkoxyalkanesulfonates, soaps, polyethoxy fatty alcohols, alkylphenols, polypropoxyglycols, polypropoxyethylenediamines, amine oxides, phosphine oxides, sulfoxides, aliphatic secondary and tertiary amines, aliphatic quaternary ammonium, phosphonium and sulfonium compounds or mixtures of the said substances.

Examples of alkaline builder salts which may be present in the compositions of the invention in an amount of e.g. 10-60% by weight comprise: water-soluble alkali metal carbonates, borates, phosphates, polyphosphates, bicarbonates and silicates, water-soluble aminopolycarboxylates, phytates, polyphosphonates and polycarboxylates, and water-insoluble aluminium silicates.

As already stated, the detergent compositions and bleaching compositions of this invention may also contain fluorescent whitening agents. All fluorescent whitening agents customarily employed in the detergent industry are suitable for this purpose. It is, however, particularly preferred to use fluorescent whitening agents of the classes of the distyrylbiphenylsulfonic acids and salts thereof and/or 4,4'-bis-(1,2,3-triazol-2-yl)-2,2'-stilbenedisulfonic acids and salts thereof, and mixtures thereof, in the detergent and bleaching compositions of this invention. If the compositions contain such fluorescent whitening agents, then these latter are present preferably in an amount of 0.005 to 1.5% by weight, most preferably of 0.01 to 0.5% by weight, based on the total weight of the composition. Suitable fluorescent whitening agents are in particular those of the formula

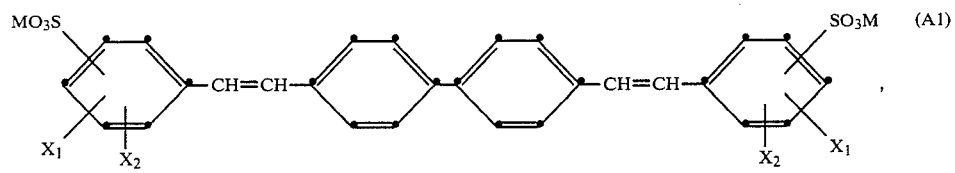

wherein $X_1$ is hydrogen, chlorine, bromine, or alkyl or alkoxy, each containing 1 to 4 carbon atoms, $X_2$ is hydrogen or alkyl having 1 to 4 carbon atoms and M is hydrogen, an alkali metal ion, ammonium ion or amine salt ion; preferably those of the formula

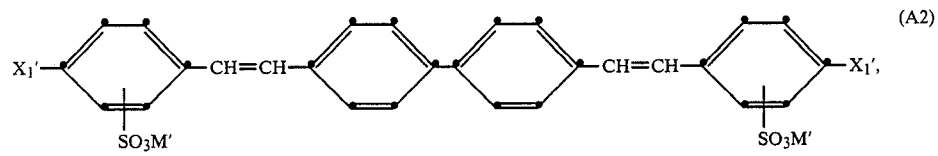

wherein $X_1'$ is hydrogen or chlorine and $M'$ is hydrogen, sodium, potassium or ammonium; and most preferably those of the formula

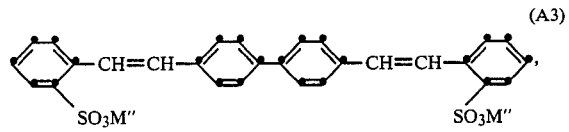

wherein $M''$ is hydrogen, sodium or potassium, and/or

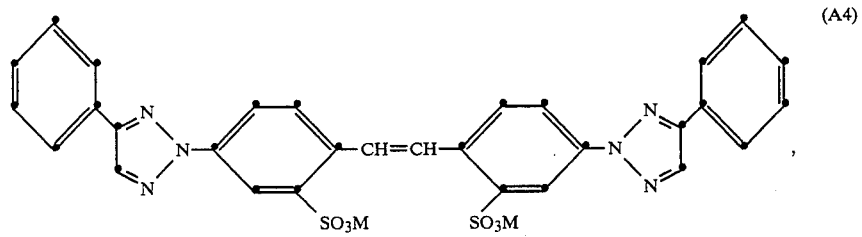

wherein M is hydrogen, an alkali metal ion, ammonium ion or amine salt ion.

The microbicidal detergent compositions of the invention preferably contain the zinc phthalocyanine or aluminium phthalocyanine compounds in an amount of 0.0005 to 1.5 percent by weight, in particular 0.005 to 1 percent by weight, based on the total detergent composition.

Moreover, microbicidal detergent compositions of the invention may have the same compositions as that described above for the detergent and soaking compositions having bleaching action.

In the following Examples, parts and percentages are by weight unless otherwise stated. In all Examples, AlPc denotes the aluminium phthalocyanine ring system and ZnPc denotes the zinc phthalocyanine ring system.

The $\lambda_{max}$ values from the absorption spectrum used for characterising the phthalocyanine compounds were measured in aqueous solution at pH 7.

EXAMPLE 1

60 parts of monochloroaluminium phthalocyanine are well stirred into 260 parts by volume of chlorosulfonic acid. The temperature is kept at 20°-25° C. by external cooling. The reaction mixture is first stirred for half an hour at room temperature and the temperature is then raised to 110° to 115° C. over a period of one hour. After half an hour, the reaction temperature is increased to 130° to 135° C. over a period of one hour and maintained for four hours. The reaction mixture is then cooled to 70° to 75° C. and treated with 125 parts by volume of thionyl chloride over a period of 45 minutes. The reaction mixture is stirred for a further one hour at 85° to 90° C. and then left to cool to room temperature, and it is then poured into an ice/water mixture. The cold sulfochloride suspension is filtered with suction and the product is washed with ice-water until the washings are free of acid.

The sulfochloride paste obtained is suspended in 1200 parts of ice/water. To the suspension are added 21 parts of cyanamide and the pH is kept at 10 with NaOH. The reaction mixture is stirred until the pH remains constant without further addition of NaOH. The resultant solution is then evaporated to dryness, affording 148 parts of a blue powder.

50 parts of the above powder are dissolved in 500 parts of water and the solution is adjusted to pH 2 with conc. hydrochloric acid and evaporated to dryness. The residue is comminuted to a fine powder and then stirred in 500 parts by volume of 1N hydrochloric acid. The suspension is filtered and the residue is washed with 250 parts by volume of 1N hydrochloric acid. The filter cake is stirred in 500 parts of water, the pH is adjusted to 7 with NaOH, and the solution is evaporated to dryness, affording 32 parts of a blue powder.

The compound so obtained has the formula

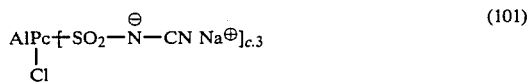

($\lambda_{max}=675$ nm).

EXAMPLE 1.1

The procedure of Example 1 is repeated, replacing monochloroaluminium phthalocyanine by an equivalent amount of an unsubstituted aluminium phthalocyanine, to give 29 parts of the compound of the formula

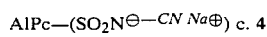 (102)

in the form of a blue powder with $\lambda_{max}=675$ nm.

EXAMPLE 1.2

The procedure of Example 1 is repeated, except that the sulfochloride paste is reacted with only 4.5 and 9 parts respectively of cyanamide, to give the compound of the formula

with $\lambda_{max}=677$ nm and the compound of the formula

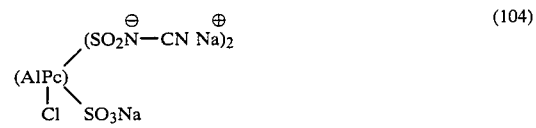

with $\lambda_{max}=677$ nm.

EXAMPLE 2

60 parts of zinc phthalocyanine are well stirred into 260 parts by volume of chlorosulfonic acid, while keeping the temperature at 20°-25° C. by external cooling. The reaction mixture is first stirred for half an hour at room temperature and the temperature is then raised to 110° to 115° C. over a period of one hour. After half an hour, the reaction temperature is increased to 130° to 135° C. over a period of one hour, and maintained for 4 hours. The reaction mixture is then cooled to 70° to 75° C. and treated with 125 parts by volume of thionyl chloride over a period of 45 minutes. The reaction mixture is stirred for a further one hour at 85° to 90° C. and then left to cool to room temperature, and it is then poured into an ice/water mixture. The cold sulfochloride suspension is filtered with suction and the product is washed with ice-water until the washings are free of acid.

The moist sulfochloride paste obtained is suspended in 1200 parts of ice/water and 21 parts of cyanamide are added, while keeping the pH at 10 with NaOH. The reaction mixture is stirred at room temperature until the pH remains constant without further addition of NaOH.

The resultant solution is clarified by filtration, then 3 parts of zinc chloride are added. The mixture is adjusted to pH 12 with NaOH and then stirred for 2 hours at 40°-45° C. The solution is adjusted to pH 1 with conc. hydrochloric acid and evaporated to dryness. The residue is finely comminuted and then stirred for 1 hour in 500 parts of water. The suspension is filtered and the filter cake is washed with a small amount of water. The residue is stirred in 1000 parts of water, the pH is adjusted to 7, and the resultant solution is evaporated to dryness, affording 55 parts of a blue powder. The compound so obtained has the formula

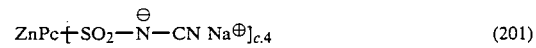

($\lambda_{max}=671$ nm)

EXAMPLE 2.1

The procedure of Example 2 is repeated, except that the sulfochloride paste is reacted with 4.5, 9 and 13.5 parts respectively of cyanamide, to give the compounds of the formulae

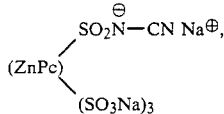 (202)

($\lambda_{max}$=670 nm),

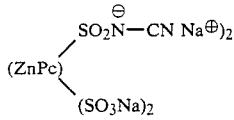 (203)

($\lambda_{max}$=670 nm) and

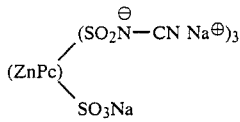 (204)

($\lambda_{max}$=670 nm).

EXAMPLE 3

The sulfochloride paste obtained in Example 1 is suspended in 1200 parts of ice/water in a stirred flask and then 100 parts by volume of conc. ammonia are added. After stirring for 2 hours, the reaction temperature is raised to 55°–60° C. and stirring is continued for 12 hours. The solution is evaporated to dryness and the residue is comminuted. The powder is stirred for 1 hour in 600 parts by volume of 1N hydrochloric acid and then isolated by filtration. The filter cake is washed with 300 parts by volume of 1N hydrochloric acid and then dried, affording 86 parts of a greenish blue powder of the probable formula

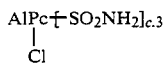 (300)

21.5 parts of the above powder are stirred in 300 parts of water. The pH is adjusted to 10 with sodium hydroxide solution and then 14 parts of methanesulfonyl chloride are added dropwise at room temperature. The reaction mixture is stirred for 2 hours at 20°–25° C. and then for 2 hours at 60° C., while keeping the pH at 10 by the dropwise addition of NaOH. The resultant solution is evaporated to dryness. The residue is comminuted and the powder is stirred in 300 parts by volume of 2N hydrochloric acid and then isolated by filtration. The filter cake is washed with 100 parts by volume of 2N hydrochloric acid and stirred once more in 300 parts of water. The pH is adjusted to 7 with NaOH and the solution is evaporated to dryness, affording 24 parts of the compound of the formula

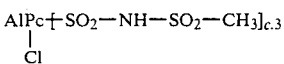 (301)

($\lambda_{max}$=673/637 nm).

EXAMPLE 3.1

The procedure of Example 3 is repeated, except that the compound of the formula (300) is reacted with only 3 and 6 parts respectively of methanesulfonyl chloride, to give the compounds of the formulae

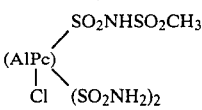 (302)

($\lambda_{max}$=637/679 nm) and

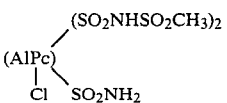 (303)

($\lambda_{max}$=637/675 nm)

EXAMPLE 3.2

The procedure of Example 3 is repeated, using instead of methanesulfonyl chloride 15 parts, 6.4 parts and 3.2 parts of p-toluenesulfonyl chloride dissolved respectively in 60, 25 and 12 parts of acetone, to give the compounds of the formulae

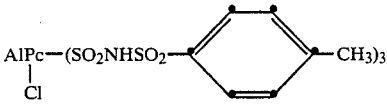 (304)

($\lambda_{max}$=677 nm),

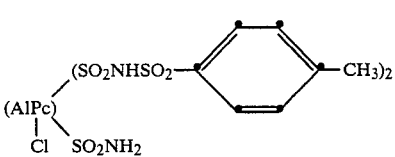 (305)

($\lambda_{max}$=677 nm), and

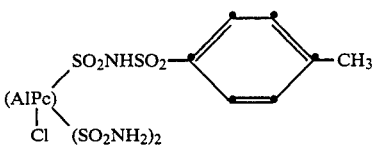 (306)

($\lambda_{max}$=676 nm).

EXAMPLE 3.3

The sulfochloride paste obtained in Example 1 is suspended in 1200 parts of ice/water and 26 parts of p-toluenesulfonamide are added. The pH of the reaction mixture is kept at 10–11 with sodium hydroxide solution. The reaction temperature is allowed to rise to 20°–25° C., then the batch is heated to 50°–55° C. until no more sodium hydroxide is consumed. The reaction solution is cooled to 25° C., adjusted to pH 7.5 with hydrochloric acid, and then clarified by filtration. The filtrate is evaporated to dryness, affording 151 parts of the sodium salt of the compound of the formula

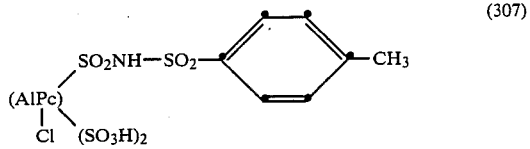
(307)

in the form of a blue powder with $\lambda_{max}=676$ nm.

EXAMPLE 3.4

The procedure of Example 3.3 is repeated using the sulfochloride paste of Example 2 instead of that of Example 1, giving 101 parts of the sodium salt of the compound of the formula

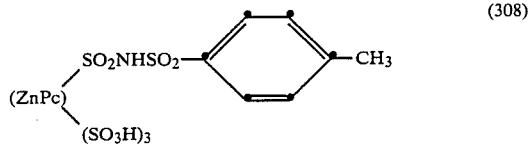
(308)

in the form of a blue powder with $\lambda_{max}=629$ nm.

EXAMPLE 4

The sulfochloride paste obtained in Example 2 is suspended in 1200 parts of ice/water in a stirred flask and then 100 parts by volume of conc. ammonia are added. After stirring for 2 hours, the reaction temperature is raised to 55°–60° C. and stirring is continued for 12 hours. The solution is evaporated to dryness and the residue is comminuted. The powder is stirred for 1 hour in 600 parts by volume of 1N hydrochloric acid and then isolated by filtration. The filter cake is washed with 300 parts by volume of 1N hydrochloric acid and then dried, affording a greenish blue powder of the probable formula $$ZnPc\{SO_2-NH_2]_{c.4} \qquad (400)$$

17.5 parts of the above zinc phthalocyaninesulfonamide are stirred in 300 parts of water. The pH is adjusted to 11 with NaOH, and 22 parts of p-toluenesulfonyl chloride are added dropwise in portions at 80°–90° C., while keeping the pH at 10–11 by the dropwise addition of NaOH. After stirring for 2 hours, the solution is cooled to 40°–45° C. and the pH is adjusted to 12 with NaOH. Then 1 part of zinc chloride is added and stirring is continued for a further 2 hours at 40°–45° C. The solution is then adjusted to pH 0.5 with hydrochloric acid and the precipitated product is isolated by filtration and washed with dilute hydrochloric acid. The filter cake is suspended in 300 parts of water and the pH is adjusted to 7.5 with NaOH. The resultant solution is evaporated to dryness, affording 20 parts of the compound of the formula

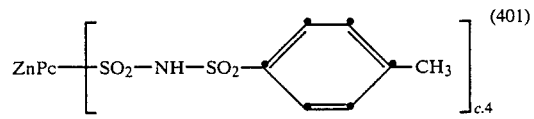
(401)

($\lambda_{max}=628$ nm).

EXAMPLE 4.1

The procedure of Example 4 is repeated, except that the compound of the formula (400) is reacted with only 11 parts of p-toluenesulfonyl chloride, to give the compound of the formula

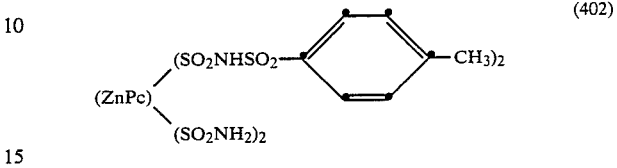
(402)

($\lambda_{max}=629$ nm).

EXAMPLE 4.2

The procedure of Example 4 is repeated, except that the compound of the formula (400) is reacted with 8 parts of methanesulfonyl chloride, to give the compound of the formula

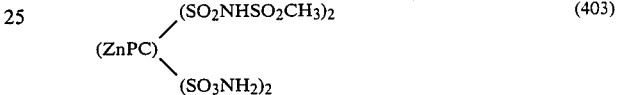
(403)

($\lambda_{max}=627$ nm).

EXAMPLE 5

The sulfochloride paste obtained in Example 1 is suspended in 1200 parts of ice/water and the pH is adjusted to 6.5 with NaOH. Then 20 parts of hydrazine hydrate are added and the reaction temperature is allowed to rise to 20°–25° C. while keeping the pH between 6.5 and 7.5 by the dropwise addition of NaOH, whereupon vigorous evolution of nitrogen is observed. Sodium hydroxide solution is added after 2 hours until the pH is 10 and the reaction mixture is stirred for 10 hours. The solution is then adjusted to pH 1 with conc. hydrochloric acid. The precipitated product is isolated by filtration and suspended in 1000 parts of water. The pH is adjusted to 7.5 with NaOH and the solution is evaporated to dryness, affording 132 parts of the sodium salt of the compound of the formula

(501)

($\lambda_{max}=682$ nm).

EXAMPLE 5.1

The procedure of Example 5 is repeated, except that the sulfochloride paste is reacted with only 10 and 5 parts respectively of hydrazine hydrate, to give the sodium salts of the compounds of the formulae

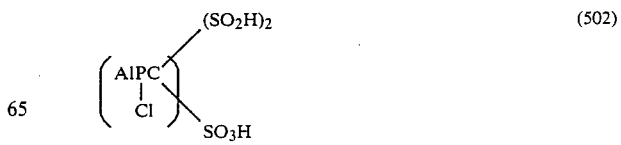
(502)

($\lambda_{max}=680$ nm) and

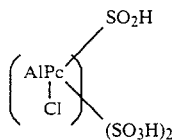 (503)

($\lambda_{max} = 679$ nm).

EXAMPLE 5.2

The procedure of Example 5 is repeated, using the sulfochloride paste of Example 2 (zinc phthalocyaninesulfochloride) instead of that of Example 1 and reacting it with 20, 15, 10 and 5 parts respectively of hydrazine hydrate, to give the sodium salts of the compounds of the formulae

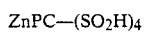 (504)

($\lambda_{max} = 634$ nm),

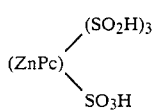 (505)

($\lambda_{max} = 633$ nm),

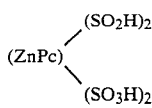 (506)

($\lambda_{max} = 633$ nm) and

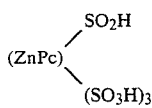 (507)

($\lambda_{max} = 632$ nm).

EXAMPLE 6

The monochloroaluminium phthalocyanine used as starting material in Examples 1, 3 and 5 may be prepared as follows:

(a) An autoclave is charged with 128 g of phthalodinitrile, 40 g of AlCl$_3$ and 650 g of 1,2-dichlorobenzene. After scavenging with nitrogen, the reaction mixture is heated for 26 hours to 170° C. After cooling and dearating, the suspension is stirred into 400 ml of water containing 100 g of trisodium phosphate. The batch is then evaporated to dryness in a rotary evaporator and the crude product is stirred in 750 ml of water. After addition of 60 g of 50% NaOH, heating to 75° C. and keeping this temperature for 2 hours, the crude product is isolated by filtration and the filter cake is stirred in 500 ml of water containing 80 g of 32% HCl (2 hours at 90°–95° C.). The product is filtered hot and washed, to give aluminium phthalocyanine which contains, per mole, about 1 mole of chlorine (monochloroaluminium phthalocyanine).

(b) In a stirred flask, a mixture of 118 parts of urea, 20 parts of 4-chlorophthalic acid, 44.4 parts of phthalic anhydride, 27 parts of xylenesulfonic acid (mixture of isomers), 1 part of ammonium molybdate, 15 parts of aluminium chloride and 200 parts of volume of trichlorobenzene (mixture of isomers) is well stirred, heated over 3 hours to 195°–205° C. and stirred at this temperature for 16 hours. After cooling, 500 parts by volume of isopropanol are added to the mixture, which is briefly stirred. The suspension is then filtered with suction and the residue is washed with 500 parts by volume of isopropanol, taken up in 800 parts by volume of dilute NaOH. The solution is stirred for 2 hours at 80°–90° C., filtered, and the filter cake is washed with warm water. The same procedure is then carried out in dilute hydrochloric acid and the pigment obtained is washed free from acid with warm water and dried, affording about 50 g of monochloroaluminium phthalocyanine in the form of a blue powder.

EXAMPLE 7

Test of activity against bacteria

Method:

A suspension of *Staphylococcus aureus* ATCC 6538 bacteria, containing a defined amount of bacteria per ml, is added to an aqueous solution which contains the compound of the formula (101), (201), (301) or (401) in a concentration of 0.01, 0.1 and 1.0 ppm. This test suspension is in a glass beaker under a water-cooled glass plate, in order to prevent warming as a result of the subsequent irradiation. Irradiation is then carried out for 5, 10, 20, 30 or 60 minutes with an incandescent lamp or an infra-red lamp ("Weiss" infra-red lamp, Philips IR, 250 W, Type 13372 E/06) which is mounted 20 cm above the surface of the suspension. The number of bacteria is then determined in conventional manner by parallel counts. The respective reduction of bacteria is calculated in powers of ten according to the formula $$\bar{x} = -\log_{10} \frac{N}{N_o},$$

where $N_o$ is the initial number of bacteria and N is the number of bacteria surviving.

The results show that all 4 compounds tested reduce the number of bacteria by $10^2$ to $10^6$, depending on the concentration and the length of exposure.

EXAMPLE 8

Test of disinfecting action on textiles

A piece of cotton fabric is stretched on a metal rack and inoculated with a test suspension (containing a compound of the formula (101), (201), (301) or (401) and a strain of test bacteria) described in Example 7. The metal rack, which is connected to a motor, is then rotated and irradiated with an infra-red lamp. A glass plate, which is cooled with running water in order to prevent warming of the piece of fabric, is positioned between the lamp and the piece of fabric. In a parallel test procedure, a piece of fabric to which no microbicidal compound has been applied, is treated under the same experimental conditions. After irradiation for 1 hour, the number of bacteria are determined quantitatively and the reduction in bacteria effected by the particular phthalocyanine is established. The action against *Staphylococcus aureus* ATCC 6538 was tested. The same reduction as in Example 7 was found.

EXAMPLE 9

Disinfection of surfaces

Enamelled tiles measuring 4×4 cm are inoculated with a suspension of *Staphylococcus aureus* ATCC 6538 bacteria, such that about $10^5$ bacteria are uniformly distributed over the surface of one tile. An aqueous solution containing 1 ppm of the compound of the formula (101), (201), (301) or (401) is then sprayed onto the surface. The surface is then irradiated for 30 or 45 minutes with an incandescent lamp (250 W, distance: 20 cm). After this time, samples are taken by staining in Rodac dishes. No further growth of the bacteria can be observed after 45 minutes on treatment with the test compounds.

EXAMPLE 10

Disinfection of an effluent from a sewage purification plant

A sample of slurry is taken from a laboratory sewage purification plant and filtered through a filter paper. One of each of the phthalocyanine compounds to be tested, of the formulae (101), (201), (301) or (401), is added to the filtrate, which contains about $10^6$ germs/ml, until its concentration in the filtrate is 1 ppm. The filtrate is then irradiated with standard light of 380-730 nm, 300 mW/cm². After various intervals of time, the remaining number of bacteria is determined. After only 45 minutes, there are no longer any staphylococci present. After a longer irradiation time (1 hour to several hours), the number of the other bacteria present in the filtrate also decreases markedly.

EXAMPLE 11

Disinfection of swimming pools

Swimming pools each having a capacity of 5000 liters of water are set up in the open. The water of one pool is treated with one of each of the compounds of the formulae (101), (201), (301) or (401) in a concentration of 0.5 ppm. At intervals of 1-5 days, water samples are taken and the number of bacteria is determined quantitatively. In the microbiological test, (a) the total number of bacteria and (b) the number of coliform germs are determined.

Result: In a pool which did not contain any of the tested phthalocyanines compounds, the coliform germs replicate to $2-3.10^1$ bacteria/100 ml. In a pool containing the active ingredient, no coliform bacteria are detected up to the 16th day of the experiment.

For a further test, a suspension of bacteria containing *Staphylococcus aureus* ATCC 6538 and *Escherichia coli* ATCC 11229, each in an amount of 50 bacteria per 100 ml of pool capacity, is added to the water on the 16th day of the experiment. Immediately after the introduction of the bacteria, measurement shows a uniform distribution in the pool. After 24 hours, no coliform bacteria and no staphylococci are detected in the pool containing the active ingredient (100 ml samples of water taken in each case). The total number of bacteria, consisting of autochthonous germ flora (bacterial flora characteristic of the swimming pool), remained constant over the test period.

EXAMPLE 12

A tea-stained cotton fabric (*) weighing 1 g is treated at 40° C. under illumination with a 250 W infra-red lamp (**) for one hour, with stirring, with 100 ml of an aqueous wash liquor which contains 0.005% (based on the weight of the fabric) of the compound of the formula (101) and 1 g of a detergent of the following composition:

| | |
|---|---|
| sodium dodecylbenzenesulfonate | 16% |
| sodium tripolyphosphate | 43% |
| sodium silicate | 4% |
| magnesium silicate | 2% |
| fatty alcohol sulfate | 4% |
| sodium carboxymethylcellulose | 1% |
| sodium salt of ethylenediaminetetraacetic acid | 0.5% |
| sodium sulfate | 29.5% |

The piece of fabric is then rinsed and dried and visually assessed. It is found that its brightness is well above that of the stained fabric.

(*)The staining of the cotton sample is carried out as follows: 15 g of tea ("Fine Ceylon Fannings Tea") are boiled for 1 hour in 600 ml of desalinated water and then filtered. The filtered tea leaves are taken up in 400 ml of desalinated water and boiled again for 60 minutes. Both filtrates are combined and made up to 1000 ml with desalinated water. With constant agitation, 45 g of cotton fabric (bleached and mercerised) are treated at 100° C. for 2½ hours in this tea liquor, then "staining" is effected in a cooled bath for a further 16 hours. Then 5 g of sodium chloride are added to the tea liquor and treatment is carried out again for 2½ hours at 100° C. Finally, the liquor is cooled and the stained cotton is rinsed twice at 60° C. and dried at 100° C. Finally, the stained fabric is washed with a liquor containing 5 g/l of detergent (composition, see above), washed for 20 minutes at 90° C. (liquor ratio 1:20), rinsed warm and cold and dried at 100° C. in a forced draught oven.
(**)Lamp used: Philips infra-red lamp (white), 220/230 V, 250 W, with reflector, type 13372 E/06. The lamp is mounted about 15 cm above the wash liquor.

The degree of bleaching of the treated fabric is also determined by measuring the degree of whiteness (brightness value) Y (expressed in %, based on the absolute white in accordance with the C.I.E. recommendation of 1.1.1969) using a Zeiss Elrepho ® spectrophotometer. The measured values confirm the visual impression and show that the addition of the photoactivator of the formula (101) effects an increase in brightness ($\Delta Y$) of about 25% compared with a comparison fabric which is washed without photosensitiser.

Similarly good results are also obtained by using the photoactivators of the formulae (201), (301), (302) to (305), (401), (402), (403), (103), (104), (202), (203), (204) or (501) instead of that of the formula (101).

EXAMPLE 13

Five 5 g samples of a cotton fabric dyed with a brown dye (*) are put into 500 ml of a wash liquor which contain 5 g/liter of a detergent of the composition indicated in Example 12, and 0.005% of the compound of the formula (101) or (201), 0.0075% of the compound of the formula (301) or (401) or 0.01% of the compound of the formula (501) (the percentages are by weight, based on the weight of the fabric). With continuous agitation the samples to be bleached are washed at 50° C. for 120 minutes and under irradiation with an infra-red lamp as described in Example 12. The samples are then rinsed and dried and the degree of bleaching of the dried sample is then measured using a Zeiss Elrepho ® photometer (standard light type D 65, 2 degree normal observer, measuring diaphragm: $\phi=35$ mm), in the form of brightness values, expressed in %, based on the absolute white according to the CIE Recommendation of 1.1.1969. The measured brightness values, which are much higher than those of the coloured fabric before and after the washed without photoactivator, show that the stained fabric is very well bleached using the photoactivators employed in the test.

Similarly high brightness values are obtained by using compounds of the formulae (103), (104), (202), (203), (204) or (502) to (507) as photoactivators.

(*) The cotton sample is dyed as follows:

150 mg of the commercially available brown dye of the formula

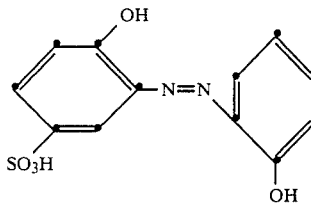

are dissolved at 50° C. in 2000 ml of water which contains 1 g of sodium carbonate. With continuous agitation, 100 g of cotton fabric (bleached and mercerised) are dyed in this dye liquor by heating the bath for 30 minutes to 90° C. Dyeing is carried out for 90 minutes at 90° C., during which time 20 g of Glauber's salt are added in four equal portions at intervals of 15 minutes.

After the dyeing operation, the fabric is rinsed twice with cold water and coppered for 20 minutes at 60° C. and at a liquor ratio of 1:20 in a bath which contains 0.75 g/liter of copper sulfate crystals and 1 ml/liter of glacial acetic acid. The fabric is then rinsed twice with cold water and dried in a hot-air oven at 100° C.

EXAMPLE 14

10 g samples of a test fabric (EMPA test fabric No. 114, obtainable from the Eidgenössische Materialprüf- und Versuchsanstalt, CH-9001 St. Gallen, Unterstrasse 11, Switzerland) stained with red wine are washed for 30 minutes at 50° C., at a liquor ratio of 1:50, in liquors which contain the following constituents:

| liquor 1: | 4 g/l of the detergent of the composition as indicated in Example 12 |
|---|---|
| liquor 2: | 4 g/l of the detergent of the composition as indicated in Example 12<br>0.0005 g of the compound of the formula (101) |
| liquor 3: | 4 g/l of the detergent of the composition as indicated in Example 12<br>0.0005 g of the compound of the formula (201) |
| liquor 4: | 4 g/l of the detergent of the composition as indicated in Example 12<br>1 g/l of sodium perborate<br>0.5 g/l of tetraacetylethylenediamine (bleach activator) |
| liquor 5: | 4 g/l of the detergent of the composition as indicated in Example 12<br>1 g/l of sodium perborate<br>0.5 g/l of tetraacetylethylenediamine<br>0.0005 g of the compound of the formula (101) |
| liquor 6: | 4 g/l of the detergent of the composition as indicated in Example 12<br>1 g/l of sodium perborate<br>0.5 g/l of tetraacetylethylenediamine<br>0.0005 g of the compound of the formula (201). |

After they have been washed, the pieces of fabric are rinsed briefly and then laid for 2 hours in the sun and repeatedly moistened. The degree of bleaching (brightness) of the samples is determined as described in Examples 12 and 13.

The results show that the samples washed in liquors 2 and 3 have substantially higher brightness values (by about 25–30%) than those which are washed in liquor 1. A comparison of the wash tests carried out in liquors 4, 5 and 6 shows that the addition of a photoactivator [here of the formula (101) or (201)] to an activated perborate bleaching liquor is able to additionally increase the brightness of the washed pieces of fabric substantially. The samples washed in liquors 5 and 6 are distinctly brighter than those washed in liquor 4.

EXAMPLE 15

A detergent slurry consisting of 50 parts of deionised water and 50 parts of a detergent of the following composition is prepared:

|  | % |
|---|---|
| linear sodium alkylbenzenesulfonate (chain length of the alkyl radical: $\overline{C}_{11.5}$) | 8.0 |
| tallow alcohol-tetradecane-ethylene glycol ether (14 oxyethylene groups) | 2.9 |
| sodium soap (chain lengths $C_{12-16}$:13–26%) $C_{18-22}$:74–87%) | 3.5 |
| sodium triphosphate | 43.8 |
| sodium silicate ($SiO_2$:$Na_2O$ = 3.3:1) | 7.5 |
| magnesium silicate | 1.9 |
| carboxymethyl cellulose | 1.2 |
| ethylenediamine tetraacetate, Na-salt | 0.2 |
| sodium sulfate | 21.2 |
| photoactivator of the formula (101) | 0.03 |
| 4,4'-bis-(2-sulfostyryl)diphenyl, sodium salt (fluorescent whitening agent) | 0.13 |
| water to make up | 100%. |

Photoactivator and fluorescent whitening agent are added to the above detergent slurry which does not yet contain these two components, with the substantial exclusion of light, and the slurry is then dried for 4 hours in a drying chamber at 80° C. under a vacuum of about 400 torr. The detergent lumps are then forced through a sieve under which there is another sieve, so that a washing powder of uniform granular size is obtained.

The test substrates employed are strips of bleached cotton fabric which are stained with fruit juices (cherry, elderberry, blackberry, red currant and bilberry), tea (see Example 12), blood (EMPA test fabric, Art. 103, Series 23) or red wine (EMPA test fabric, Art. 103, Series 23).

Test strips of the above soiled fabrics are each washed in a liquor containing 4 g/l of the above detergent at a liquor ratio of 1:20 for 30 minutes at 50° C., then rinsed briefly and hung moist on a line, where they are left to dry for 6 hours while spraying them every 40 minutes with an alkaline solution of pH 9. These wash tests are also carried out with a detergent which does not contain fluorescent whitening agent or photoactivator or both. The degree of stain removal is assessed visually. Use of the detergent without fluorescent whitening agent and photoactivator results in more or less modest stain removal. The presence of the photoactivator in the detergent (without fluorescent whitening agent) leads to very good and significant bleaching effects. Use of the fluorescent whitening agent alone (without photoactivator) results in bleaching effects which, however, are less pronounced than those obtained with the photoactivator alone. The best results in all types of staining are obtained when photoactivator and fluorescent whitening agent are both present in the detergent. An exceptionally white, strongly bleached cotton fabric is obtained in each case. The effects obtained are evaluated colorimetrically using a standardised piece of cotton which is coloured brown (see Example 13). The visually determined assessments are fully confirmed.

Results corresponding to those described above are obtained by using in the detergent of the given composition the potassium salt of 4,4'-bis-(4-phenyl-1,2,3-triazol-2-yl)-2,2'-stilbenedisulfonic acid as fluorescent whitening agent and/or one or more compounds of the formulae (201), (301) to (305), (401) to (403), (103), (104), (202) to (204) or (501) to (507) as photoactivator.

What is claimed is:

1. A phthalocyanine compound of the formula

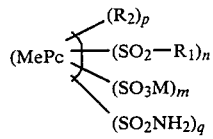

wherein MePc is the zinc or aluminum phthalocyanine ring system, M is hydrogen or the equivalent of a salt-forming cation, $R_1$ is M or a group of the formula

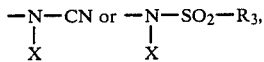

wherein X is hydrogen or ammonium or the equivalent of a monovalent, divalent or trivalent metal ion, and $R_3$ is $C_1$-$C_8$-alkyl, unsubstituted or substituted by hydroxy, alkoxy, halogen, cyano, or carbalkoxy, aminocarbonyl or dialkylamino; aryl, unsubstituted or substituted by alkyl or alkoxy, nitro, haloalkyl, halogen, alkoxycarbonyl, cyano, alkylsulfonyl, acylamino, carboxy and derivatives thereof, sulfo and derivatives thereof, acyloxy, trifluoromethyl or dialkylamino, or an unsubstituted or substituted or fused 5- or 6-membered aromatic heterocyclic ring containing one or two nitrogen, oxygen or sulfur heteroatoms which may be unsubstituted or substituted in the same manner as the aryl groups $R_3$; each $R_2$ is independently halogen, aryl or cyano, n has any value from 1 to 4, each of m and q has any value from 0 to 3 and p has any value from 0 to 4, while the sum of n+m and n+q in each case is 1 to 4 and q is only different from 0 if $R_1$ is a group of the formula

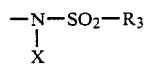

and m is 0.

2. A phthalocyanine compound of claim 1, wherein q is 0.

3. A phthalocyanine compound of claim 1, wherein M is hydrogen, an alkali metal ion, an ammonium ion or an amine salt ion, $R_2$ is a halogen atom or cyano and X is hydrogen, ammonium or an alkali metal atom.

4. A phthalocyanine compound of claim 3, wherein $R_2$ is a halogen atom and $R_3$ is $C_1$-$C_4$alkyl, $C_1$-$C_4$haloalkyl, $C_2$-$C_6$alkoxyalkyl, $C_1$-$C_4$hydroxyalkyl, $C_2$-$C_5$-cyanoalkyl, di($C_1$-$C_4$)-alkylamino($C_1$-$C_4$)alkyl or benzyl, phenyl or phenyl substituted by 1 to 3 substituents selected from the group consisting of halogen, $C_1$-$C_4$alkyl, $C_1$-$C_4$alkoxy, cyano, nitro, di($C_1$-$C_4$)alkylamino, and sulfo and carboxy and the salts thereof.

5. A phthalocyanine compound of claim 4 of the formula

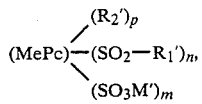

wherein $R_2'$ is chlorine, bromine or iodine, M' is hydrogen, sodium, potassium or ammonium, and $R_1'$ is hydrogen, M' or a group of the formula

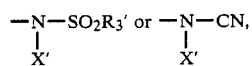

wherein X' is hydrogen, sodium, potassium or ammonium, and $R_3'$ is $C_1$-$C_4$alkyl, phenyl or $C_1$-$C_4$alkylphenyl, chlorophenyl or methoxyphenyl, and MePc, n, m and p are as defined in claim 4.

6. A phthalocyanine compound of claim 2, wherein $R_1$ is hydrogen or a group of the formula

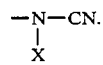

7. A phthalocyanine compound of claim 5 wherein $R_2'$ is chlorine.

8. A phthalocyanine compound of claim 2, wherein $R_1$ is a group of the formula

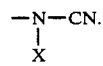

* * * * *